US00PP20986P2

(12) United States Plant Patent
Kordes

(10) Patent No.: US PP20,986 P2
(45) Date of Patent: May 11, 2010

(54) MINIATURE ROSE PLANT NAMED 'KORZANABY'

(50) Latin Name: *Rosa hybrida*
Varietal Denomination: KORzanaby

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/322,243

(22) Filed: Jan. 30, 2009

(51) Int. Cl.
*A01H 5/00* (2006.01)

(52) U.S. Cl. ..... Plt./120

(58) Field of Classification Search ..... Plt./120, Plt./119
See application file for complete search history.

(56) References Cited

OTHER PUBLICATIONS

2008/0221, European Union CVPO summary, Apr. 15, 2008, European Union.

*Primary Examiner*—Kent L Bell

(57) ABSTRACT

A new and distinct variety of miniature rose with long lasting, novel peach blend flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

SUMMARY OF THE INVENTION

Genus, species and variety denomination: The botanical classification of the new rose plant is *Rosa hybrida*, 'KORzanaby'.

BACKGROUND OF THE INVENTION

The new variety of miniature rose plant of the present invention originated from a controlled crossing made during the summer of 2003 in a breeding program between 'KORvapoco', a non-patented rose; and 'KORnilsca' described and illustrated in U.S. Plant Pat. No. 16,268 issued on Feb. 21, 2006.

As part of the rose development program, Tim-Hermann Kordes germinated the seeds from the aforementioned hybridization the following winter and conducted evaluations and observations on the resulting seedlings in a controlled environment in Offenseth-Sparrieshoop, Germany. The resulting seedlings exhibited distinctive physical and biological characteristics. The new rose plant was selected as a single plant from the seedling beds due to its superior characteristics. The new rose plant 'KORzanaby' was selected in May, 2004 from the seedling beds to be asexually propagated for further evaluation. The first asexual reproduction of 'KORzanaby' was done by rooting softwood cuttings in August, 2004 in Odense, Denmark.

The hybridization, seed production, seed germination, seedling selection, and subsequent propagations were conducted in controlled greenhouse environments. This new and distinctive miniature rose variety is named 'KORzanaby'.

This initial and other subsequent propagations conducted in controlled environments show that the foregoing and all other characteristics of 'KORzanaby' come true to form and are transmitted through succeeding generations.

SUMMARY OF THE INVENTION

The new rose plant may be distinguished from its seed parent, 'KORvapoco' by the following combination of characteristics:

1. The flower size of the seed parent is large, while the flower size of 'KORzanaby' is medium sized.
2. The flower color of the seed parent is apricot, while the flower color of 'KORzanaby' is a peach blend.

The new rose plant may be distinguished from its pollen parent, 'KORnilsca' by the following combination of characteristics:

1. The pollen parent is more compact and exhibits less vigorous growth than 'KORzanaby'.
2. The flower color of the pollen parent is pink, while the flower color of 'KORzanaby' is a peach blend.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers.

This combination of qualities is not present in prior rose cultivars. These objectives have been substantially achieved and in that distinguish 'KORzanaby' from all other varieties of which we are aware.

BRIEF DESCRIPTION OF THE DRAWING

The accompanying color illustration shows as true as is reasonably possible to obtain in color photographs of this type, the typical characteristics of the buds, flowers, leaves, and stems of 'KORzanaby'. Specifically illustrated is: a flower bud, partially opened bloom, open bloom, floral parts, sepals, juvenile foliage, stem exhibiting thorns, and leaves.

DETAILED BOTANICAL DESCRIPTION

The following is a description of 'KORzanaby', as observed in its growth in January, 2009 in a nursery in Jackson County, Oreg. on plants four months of age. Color references are made using The Royal Horticultural Society (London, England) Colour Chart, 2001 except where common terms of color are used.

For a comparison, several physical characteristics of the rose variety 'KORnilsca', a rose variety from the same inventor described and illustrated in U.S. Plant Pat. No. 16,268 and issued on Feb. 21, 2006 are compared to 'KORzanaby' in Chart 1.

CHART 1

| | 'KORzanaby' | 'KORnilsca' |
|---|---|---|
| Flower bud color | Middle zone - Red Group 50B<br>Marginal zone - Red Group 39B | Red Group 54A |
| Average size of receptacle | 6-7 mm (h) × 9-10 mm (w) | 7-8 mm (h) × 10-11 mm (w) |
| Average open bloom diameter | 30-35 mm | 50 mm |

Parents:

*Seed parent.*—'KORvapoco'.

*Pollen parent.*—'KORnilsca'.

Classification:

*Botanical classification.*—*Rosa hybrida*, 'KORzanaby'.

*Commercial classification.*—Miniature rose.

FLOWER AND FLOWER BUD

Blooming habit: Recurrent.

Flower bud:

*Size.*—Upon opening, 24–27 mm in length from base of receptacle to end of bud and 13–15 mm in diameter at its widest point.

*Bud form.*—Medium. Pointed ovoid.

*Bud color.*—As sepals first unfold, bud color is a blend of Red Group 50B (middle zone) and Red Group 39B (marginal zone). When ¼ open, the upper surface of petals is Orange Group 29C, and the lower surface is Red Group 39B and Red Group 39C.

*Sepals.*—Size: Average 23–25 mm long×5–6 mm wide. Shape: Sepals generally subulate. Sepal apex is generally cirrose. Average to strong foliaceous appendages on three of the five sepals. Base is flat at union with receptacle. Quantity: Five. Margins: Ciliate. Surface texture: Inner side: Covered in fine white hairs. Outer surface: Smooth. Stipitate glands are absent. Color: Upper surface Green Group 137A with intonations of Green Group 138B. Lower surface Green Group 137A.

Receptacle:

*Surface.*—Many fine white hairs.

*Color.*—Yellow-Green Group 144B.

*Shape.*—Funnel shaped.

*Size.*—6–7 mm (h)×9–10 mm (w).

Peduncle:

*Surface.*—With fine hairs.

*Length.*—32–35 mm average length.

*Diameter.*—2 to 2.5 mm average diameter.

*Color.*—Yellow-Green Group 144B.

Strength: Strong.

*Borne.*—Singly. 1–3 buds per flowering stem.

Flower bloom:

*Fragrance.*—None.

*Duration.*—Long lasting. A blooming plant with flowers has a commercial shelf life of 14–16 days. The blooms have a duration on the plant of approximately 8 to 12 days.

*Size.*—Medium for an 10 cm pot rose. Average flower diameter is 30–35 mm when open. Average flower depth is 20–25 mm.

*Form.*—Shape of flower when viewed from the side: Upon opening, upper part: Flat. Upon opening, lower part: Flattened convex. Open flower, upper part: Flattened convex. Open flower, lower part: Concave.

Color:

*Upon opening, petals.*—Outermost petals: Outer Side: A blend of Red Group 37A and Orange Group 29B with intonations of Red Group 50B. Inner Side: A blend of Orange Group 29B and Orange Group 29C with intonations of Red Group 39D. Innermost petals: Outer Side: A blend of Red Group 37A and Orange Group 29B. Inner Side: A blend of Orange Group 29C and Orange Group 29D.

*Upon opening, basal petal spots.*—Basal petal spot, outermost petals: Outer Side: Green-Yellow Group 1D. Inner Side: Green-Yellow Group 1C. Basal petal spot, innermost petals: Outer Side: Green-Yellow Group 1C. Inner Side: Green-Yellow Group 1B.

*After opening, petals.*—Outermost petals: Outer Side: A blend of Red Group 37A and Orange Group 29B. Inner Side: A blend of Orange Group 29B and Orange Group 29C. Innermost petals: Outer Side: A blend of Red Group 37A and Orange Group 29B. Inner Side: A blend of Orange Group 29C and Orange Group 29D.

*After opening, basal petal spots.*—Basal petal spot, outermost petals: Outer Side: Green-Yellow Group 1D. Inner Side: Green-Yellow Group 1C. Basal petal spot, innermost petals: Outer Side: Green-Yellow Group 1C. Inner Side: Green-Yellow Group 1B.

*Variegations.*—None.

General tonality: On open flower a blend of Orange Group 29A and Red 37A. No change in the general tonality at the end of the $6^{th}$ day. Afterwards, general tonality is Orange Group 29C and Red 37C.

Petals:

*Petal count.*—Approximately 25–30 petals under normal conditions.

*Petal reflex.*—Petals reflex slightly.

*Petal edge.*—Entire.

*Petal shape.*—Deltoid. Apex shape is round. Shape of base is acute.

*Petal size.*—22–24 mm long; 22–26 mm wide.

*Thickness.*—Average.

*Petal arrangement.*—Generally in a regular pattern with overlapping edges.

Petaloids: Present.

*Petaloid count.*—Average of 10–15 per flower.

*Petaloid edge.*—Ruffled.

*Petaloid texture.*—Rough.

*Petaloid shape.*—Base: acute. Apex: rounded with indent at center of margin.

*Petaloid size.*—Petaloids are 10–13 mm long and 7–11 mm wide.

*Petaloid color.*—Color of inner side is Yellow Group 18B. Color of outer side is Red Group 39B.

Reproductive organs:

*Pistils.*—Approximately 35–40 present. Stigmas: Location: Slightly superior in position to anthers. Color: Green-Yellow Group 1C. Styles: Length: 3–4 mm long. Color: Green-Yellow Group 1D.

*Stamens.*—Approximately 40–45 on average and regularly arranged. Anthers: Size: 2 mm long. Color: Yellow Group 4A. Pollen: Absent. Filaments: Color: Yellow-Orange Group 14A. Length: 2–3 mm.

THE PLANT

*Plant growth.*—Moderately vigorous. Compact to bushy habit. When grown as an 8–11 cm pot plant, the average height of the plant itself is 18–20 cm and the average width is 18–20 cm.

*Stems.*—Stem color: Young wood: Yellow-Green Group 144A. Older wood: Green Group 138A. Stem surface: Young wood: Smooth. Older wood: Smooth.

*Prickles.*—Present. Incidence: 10–12 per 10 cm of stem. Size: Average length: 3–4 mm. Color: Immature prickles: Greyed-Yellow Group 162B. Mature prickles: Greyed-Yellow Group 162B. Senescing to Greyed-Yellow Group 164A. Shape: Concave. Anthocyanin: Present. Color: Greyed-Red Group 182B.

*Leaves and leaflets.*—Normally 3–5 leaflets on normal leaves in middle of the stem. Venation pattern: Pyramidal net pattern. Leaf size: 85–90 mm (l)×60–65 mm (w). Quantity: Average. Texture: Upper side of leaflet: Glossy. Smooth. Under side of leaflet: Matte. Rough. Color, mature foliage: Upper Leaf Surface: Green Group 137A. Lower Leaf Surface: Yellow-Green Group 147B. Color, juvenile foliage: Upper Leaf Surface: Green Group 136A. Lower Leaf Surface: Yellow-Green Group 147B. Anthocyanin intonation: Present. Color: Greyed-Red Group 178A. Location: intonations present on entire leaf of plants grown under high light conditions.

*Stipules.*—Size: 10–11 mm long. 5–6 mm between the tips of the stipule. Main body of stipule 3–4 mm in width. Shape: Longitudinally flanged or winged along middle. Stipule color: Green Group 137A. Anthocyanin Greyed-Red Group 182A. Stipitate glands: Few on margins. Margins: Serrated. With few stipitate glands.

*Petiole.*—Length: 12–15 mm. Diameter: 1–1.5 mm. Petiole color: Green Group 137A. Anthocyanin present on juvenile tissue. Greyed-Red Group 182A. Underneath: An occasional prickle underneath. Margins: A few short, white hairs. Stipitate glands: Absent.

*Petiole rachis.*—Length: 13–15 mm. Diameter: 1–1.5 mm. Color: Green Group 137A. Anthocyanin present on juvenile tissue. Greyed-Red Group 182A. Prickles: An occasional prickle underneath. Margins: Short, white hairs. Stipitate glands: Absent.

*Leaflets.*—Size: Average size of the terminal leaflet is 35–40 mm (l)×18–20 mm (w). Shape: Ovate. Base: Ovate. Apex: Acute. Surface: Upper side: Glossy. Lower side: Matte. Margins: Finely serrated. Texture: Leathery.

Hips/seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to powdery mildew and *Botrytis* under normal growing conditions.

I claim:

1. A new and distinct variety of miniature rose plant characterized by the following combination of characteristics:

(a) Forms abundant, attractive long lasting peach blend flowers;

(b) Exhibits a compact and bushy growth habit;

(c) Is suited for growing in greenhouse in pots from softwood cuttings, and;

(d) Exhibits durable flowers and foliage suitable for distribution in the floral industry; substantially as herein illustrated and described.

* * * * *

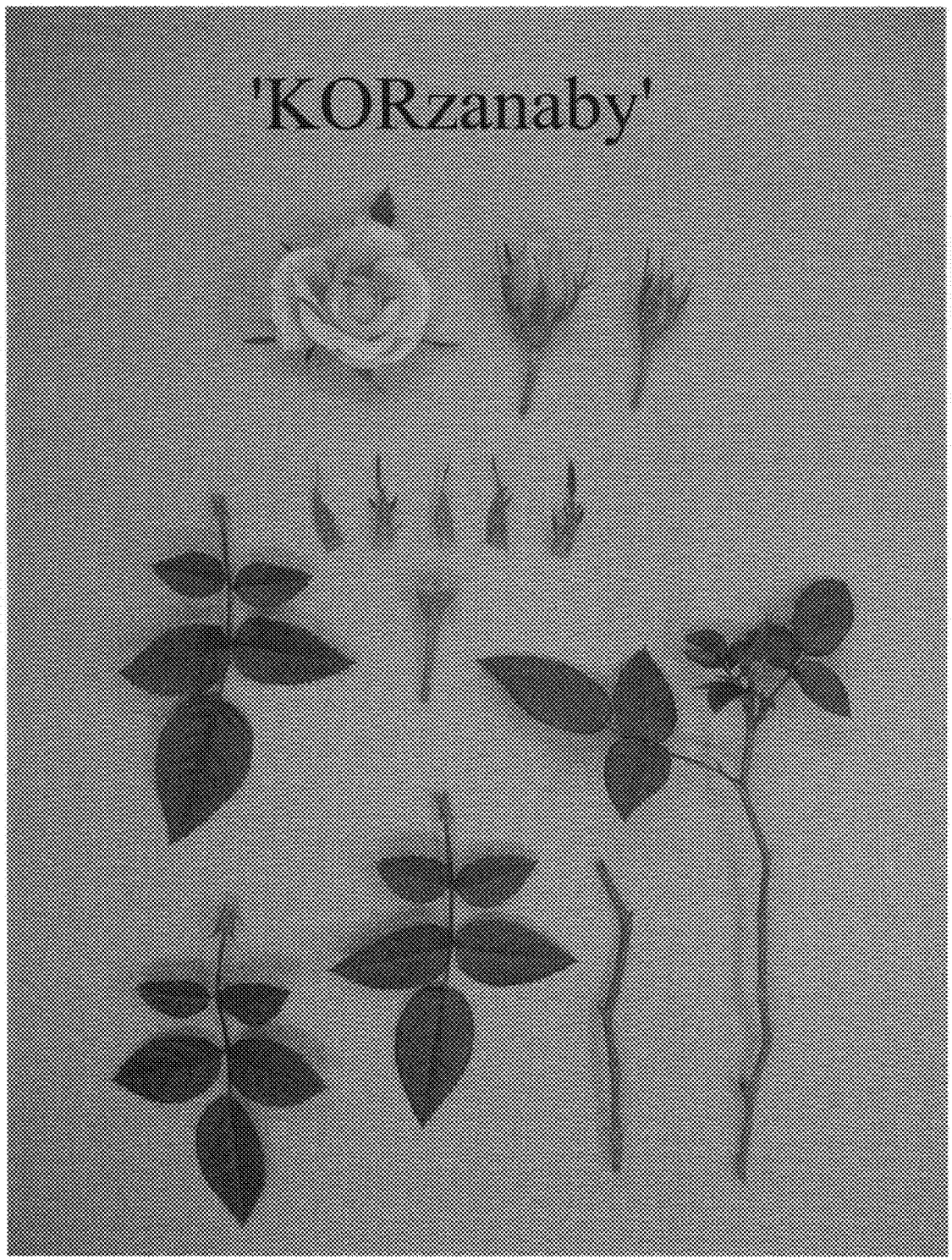
'KORzanaby'